United States Patent
Frewin et al.

(10) Patent No.: US 9,211,401 B2
(45) Date of Patent: *Dec. 15, 2015

(54) CUBIC SILICON CARBIDE IMPLANTABLE NEURAL PROSTHETIC

(75) Inventors: Christopher Leroy Frewin, Tampa, FL (US); Stephen E. Saddow, Odessa, FL (US); Edwin Weeber, Apollo Beach, FL (US)

(73) Assignee: University of South Florida, Tampa, FL (US)

( * ) Notice: Subject to any disclaimer, the term of this patent is extended or adjusted under 35 U.S.C. 154(b) by 829 days.

This patent is subject to a terminal disclaimer.

(21) Appl. No.: 13/479,631

(22) Filed: May 24, 2012

(65) Prior Publication Data
US 2012/0232631 A1 Sep. 13, 2012

Related U.S. Application Data

(63) Continuation of application No. PCT/US2010/058376, filed on Nov. 30, 2010.

(60) Provisional application No. 61/265,148, filed on Nov. 30, 2009.

(51) Int. Cl.
*A61N 1/00* (2006.01)
*A61N 1/05* (2006.01)
(Continued)

(52) U.S. Cl.
CPC .......... *A61N 1/0529* (2013.01); *A61B 5/04001* (2013.01); *C23C 16/325* (2013.01); *Y10T 29/49194* (2015.01)

(58) Field of Classification Search
CPC ................................. A61B 5/04; H01R 43/00
USPC .................................................. 607/377, 373
See application file for complete search history.

(56) References Cited

U.S. PATENT DOCUMENTS

| 4,461,304 A | 7/1984 | Kuperstein |
| 5,855,801 A | 1/1999 | Lin et al. |

(Continued)

FOREIGN PATENT DOCUMENTS

| WO | 0172201 A2 | 10/2001 |
| WO | 2009012502 A1 | 1/2009 |

OTHER PUBLICATIONS

V. Y. Aristov, et al., "Graphene Synthesis on Cubic SiC/Si Wafers. Perspectives for Mass Production of Graphene-Based Electronic Devices," Nano Letters, vol. 10, pp. 992-995, Mar 2010.

(Continued)

*Primary Examiner* — Catherine Voorhees
*Assistant Examiner* — Roland Dinga
(74) *Attorney, Agent, or Firm* — Michele L. Lawson; Smith & Hopen, P.A.

(57) ABSTRACT

An implantable neuronal prosthetic and method of manufacture thereof includes at least one elongated electrode shank adapted for arrangement in the brain having at least one electrode contact disposed on its surface and arranged to electrically couple with said brain. The at least one elongated electrode shank is formed form a single crystal cubic silicon carbide. An insulation layer of amorphous, polycrystalline, or single crystal silicon carbide is disposed over the elongated electrode shank; the insulation layer of amorphous, polycrystalline, or single crystal silicon carbide is removed from the at least one electrode contact. Signal control electronics are attached to the at least one elongated electrode shank and are in electrical communication with the at least one electrode contact. In an embodiment, a plurality of the at least one elongated electrode shanks are arranged into a matrix.

10 Claims, 2 Drawing Sheets

(51) Int. Cl.
A61B 5/04 (2006.01)
C23C 16/32 (2006.01)

(56) References Cited

U.S. PATENT DOCUMENTS

| | | | |
|---|---|---|---|
| 6,016,449 A * | 1/2000 | Fischell et al. | 607/45 |
| 6,480,743 B1 | 11/2002 | Kirkpatrick et al. | |
| 6,829,498 B2 | 12/2004 | Kipke et al. | |
| 6,952,687 B2 | 10/2005 | Andersen et al. | |
| 6,993,392 B2 | 1/2006 | Nicolelis et al. | |
| 7,015,142 B2 | 3/2006 | DeHeer et al. | |
| 7,107,104 B2 | 9/2006 | Keravel et al. | |
| 7,120,486 B2 | 10/2006 | Leuthardt et al. | |
| 7,548,775 B2 | 6/2009 | Kipke et al. | |
| 2004/0106953 A1* | 6/2004 | Yomtov et al. | 607/3 |
| 2006/0134096 A1 | 6/2006 | Petrik | |
| 2006/0293578 A1 | 12/2006 | Rennaker, II | |
| 2007/0060815 A1 | 3/2007 | Martin et al. | |
| 2007/0293910 A1 | 12/2007 | Strother et al. | |
| 2009/0020764 A1 | 1/2009 | Anderson et al. | |
| 2009/0169919 A1 | 7/2009 | Garcia et al. | |
| 2009/0248113 A1 | 10/2009 | Nimer et al. | |
| 2009/0299167 A1* | 12/2009 | Seymour | 600/393 |

OTHER PUBLICATIONS

D. F. Williams, "On the mechanisms of biocompatibility," Biomaterials, vol. 29, pp. 2941-2953, Jul. 2008.
J. J. Jacobs, et al., "Corrosion of metal orthopaedic implants," J Bone Joint Surg Am, vol. 80, pp. 268-82, Feb. 1998.
J. A. Porter and J. A. Von Fraunhofer, "Success or failure of dental implants? A literature review with treatment considerations," Gen Dent, vol. 53, pp. 423-32; Nov.-Dec. 2005.
E. R. Edelman and C. Rogers, "Stent-versus-stent equivalency trials—Are some stents more equal than others?," Circulation, vol. 100, pp. 896-898, Aug. 31, 1999.
L. L. Hench and J. Wilson, "Biocompatibility of Silicates for Medical Use," Ciba Foundation Symposia, vol. 121, pp. 231-246, 1986.
I. Willner and B. Willner, "Biomaterials integrated with electronic elements: en route to bioelectronics," Trends in Biotechnology, vol. 19, No. 6, pp. 222-230, Jun. 2001.
G. S. Wilson and R. Gifford, "Biosensors for real-time in vivo measurements," Biosensors & Bioelectronics, vol. 20, pp. 2388-2403, Jun. 15, 2005.
S. F. Cogan, "Neural stimulation and recording electrodes," Annu Rev Biomed Eng, vol. 10, pp. 275-309, 2008.
W. M. Chardack, et al., "Experimental Observations and Clinical Experiences with the correction of complete heart block by an Implantable Self-Contained Pacemaker," Trans Am Soc Artif Intern Organs, vol. 7, pp. 286-295, 1961.
W. Greatbatch, "Implantable Cardiac Pacemakers," Proceedings of the Institute of Radio Engineers, vol. 48, pp. 386, 1960.
P. G. Whitten, et al., "Free standing carbon nanotube composite bio-electrodes," Journal of Biomedical Materials Research Part B—Applied Biomaterials, vol. 82B, pp. 37-43, Jul. 2007.
C. Berger, et al., "Ultrathin epitaxial graphite: 2D electron gas properties and a route toward graphene-based nanoelectronics," Journal of Physical Chemistry B, vol. 108, pp. 19912-19916, Dec. 30, 2004.
K. S. Novoselov, et al., "Electric field effect in atomically thin carbon films," Science, vol. 306, pp. 666-669, Oct. 22, 2004.
A. K. Geim and K. S. Novoselov, "The rise of graphene," Nature Materials, vol. 6, pp. 183-191, Mar. 2007.
K. S. Kim, et al., "Large-scale pattern growth of graphene films for stretchable transparent electrodes," Nature, vol. 457, pp. 706-710, Feb. 5, 2009.
H. Chen, et al., "Mechanically strong, electrically conductive, and biocompatible graphene paper," Advanced Materials, vol. 20, pp. 3557-3561, Sep. 17, 2008.
P. W. Sutter, et al. , "Epitaxial graphene on ruthenium," Nature Materials, vol. 7, pp. 406-411, May 2008.

N. P. Guisinger, et al., "Atomic-scale investigation of graphene formation on 6H-SiC(0001)," Journal of Vacuum Science & Technology A, vol. 26 No. 4, pp. 932-937, Jul.-Aug. 2008.
J. Hass, et al., "The growth and morphology of epitaxial multilayer graphene," Journal of Physics-Condensed Matter, vol. 20, pp. 1-27, Aug. 13, 2008.
P. Sutter, "Epitaxial Graphene How silicon leaves the scene," Nature Materials, vol. 8, pp. 171-172, Mar. 2009.
C. Riedl, et al., "Quasi-Free-Standing Epitaxial Graphene on SiC Obtained by Hydrogen Intercalation," Physical Review Letters, vol. 103, pp. 1-4, Dec. 11, 2009.
C. Virojanadara, et al., "Buffer layer free large area bi-layer graphene on SiC(0001)," Surface Science, vol. 604, pp. L4-L7, Jan. 15, 2010.
I. W. Frank, et al., "Mechanical properties of suspended graphene sheets," Journal of Vacuum Science & Technology B, vol. 25, No. 6, pp. 2558-2561, Nov. 2007.
W. R. Yang, et al., "Carbon Nanomaterials in Biosensors: Should You Use Nanotubes or Graphene?," Angewandte Chemie-International Edition, vol. 49, pp. 2114-2138, 2010.
X. Wang, et al., "Transparent, conductive graphene electrodes for dye-sensitized solar cells," Nano Letters, vol. 8, No. 1, pp. 323-327, Jan. 2008.
M. Y. Han, et al., "Energy band-gap engineering of graphene nanoribbons," Physical Review Letters, vol. 98, pp. 206805-1-206805-4, May 18, 2007.
S. Y. Zhou, et al., "Substrate-induced bandgap opening in epitaxial graphene," Nature Materials, vol. 6, pp. 770-775, Oct. 2007.
T. Ohta, et al, "Controlling the electronic structure of bilayer graphene," Science, vol. 313, pp. 951-954, Aug. 18, 2006.
Y. Wang, et al., "Application of graphene-modified electrode for selective detection of dopamine," Electrochemistry Communications, vol. 11, pp. 889-892, Apr. 2009.
M. D. Stoller, et al., "Graphene-Based Ultracapacitors," Nano Letters, vol. 8, No. 10, pp. 3498-3502, Oct. 2008.
M. Pumera, "Electrochemistry of Graphene: New Horizons for Sensing and Energy Storage," Chemical Record, vol. 9, pp. 211-223, 2009.
S. R. C. Vivekchand, et al., "Graphene-based electrochemical supercapacitors," Journal of Chemical Sciences, vol. 120, No. 1, pp. 9-13, Jan. 2008.
S. P. Pang, et al., "Patterned Graphene Electrodes from Solution-Processed Graphite Oxide Films for Organic Field-Effect Transistors," Advanced Materials, vol. 21, pp. 3488-3491, Sep. 11, 2009.
D. R. Merrill, et al., "Electrical stimulation of excitable tissue: design of efficacious and safe protocols," Journal of Neuroscience Methods, vol. 141, pp. 171-198, Feb. 15, 2005.
V. Lovat, et al., "Carbon nanotube substrates boost neuronal electrical signaling," Nano Letters, vol. 5, No. 6, pp. 1107-1110, Jun. 2005.
B. S. Harrison and A. Atala, "Carbon nanotube applications for tissue engineering," Biomaterials, vol. 28, pp. 344-353, Jan. 2007.
E. Jan and N. A. Kotov, "Successful differentiation of mouse neural stem cells on layer-by-layer assembled single-walled carbon nanotube composite," Nano Letters, vol. 7, No. 5, pp. 1123-1128, May 2007.
S. Agarwal, et al., "Interfacing Live Cells with Nanocarbon Substrates," Langmuir, vol. 26, No. 4, pp. 2244-2247, Feb. 16, 2010.
J. Kedzierski, et al., "Epitaxial graphene transistors on SIC substrates," IEEE Transactions on Electron Devices, vol. 55, pp. 2078-2085, Aug. 2008.
J. S. Moon, et al., "Epitaxial-Graphene RF Field-Effect Transistors on Si-Face 6H-SiC Substrates," IEEE Electron Device Letters, vol. 30, No. 6, pp. 650-652, 2009.
J. Vidal, "Toward direct brain-computer communication", in Annual Review of Biophysics and Bioengineering, L. J. Mullins, Ed. Palo Alto, CA, USA: Annual Reviews, Inc., 1973, pp. 157-180.
M. A. Lebedev, and M. A. L. Nicolelis, "Brain-machine interfaces: past, present and future", Trends Neurosci., vol. 29, No. 9, pp. 536-546, 2006.
K. D. Wise, A. M. Sodagar, Y. Yao, M. N. Gulari, G. E. Perlin, and K. Najafi, "Microelectrodes, microelectronics, and implantable neural microsystems", Proceedings of the IEEE, vol. 96, No. 7, pp. 1184-1202, 2008.

(56) References Cited

OTHER PUBLICATIONS

C. Richards-Grayson, R. S. Shawgo, and A. M. Johnson, "A bioMEMS review: MEMS technology for physiologically integrated devices", Proceedings of the IEEE, vol. 92, No. 1, pp. 6-21, 2004.

N. C. Berchtold, C. W. Cotman, "Evolution in the conceptualization of dementia and Alzheimer's disease: Greco-Roman period to the 1960s". Neurobiol. Aging vol. 19, No. 3, pp. 173-189, 1998.

J. Jankovic, "Parkinson's disease: clinical features and diagnosis". J. Neurol. Neurosurg. Psychiatr. vol. 79, No. 4, pp. 368-376, 2008.

C. E. Schmidt and J. B. Leach, "Neural Tissue Engineering: Strategies for Repair and Regeneration", Annu. Rev. Biomed. Eng., vol. 5, pp. 293-347, 2003.

M. Santos, J. R. Fernandes, and M. S. Pieda, "A Microelectrode Stimulation System for a Cortical Neuroprosthesis", Conference on Design of Circuits and Integrated Systems, Barcelona, Spain, 2006.

Kennedy, P. R., and Bakay, R. A. E., "Restoration of neural output from a paralyzed patient by a direct brain connection", NeuroReport 9, pp. 1707-1711, 1998.

J. K. Chapin, K. A. Moxon, R. S. Markowitz, and M. A. L. Nicolelis, "Real-time control of a robot arm using simultaneously recorded neurons in the motor cortex", Nature Neuroscience, vol. 2, No. 7, pp. 664-670, 1999.

S. Martinoia, P. Massobrio, M. Bove, and G. Massobrio, "Cultured neurons coupled to microelectrode arrays: circuit models, simulations and experimental data", IEEE Transactions on Biomedical Engineering, vol. 51, No. 5, pp. 859-864, 2004.

A. L. Hodgkin and A. F. Huxley, "Currents carried by sodium and potassium ions through the membrane of the giant axon of Loligo", J. Physiol. (Lond.), vol. 116, No. 4, pp. 449-472, 1952.

A. L. Hodgkin and A. F. Huxley, "The components of membrane conductance in the giant axon of Loligo", J. Physiol (Lond.), vol. 116, No. 4, pp. 473-496, 1952.

A. L. Hodgkin and A. F. Huxley, "The dual effect of membrane potential on sodium conductance in the giant axon of Loligo", J. Physiol (Lond.), vol. 116, No. 4, pp. 497-506, 1952.

A. L. Hodgkin and A. F. Huxley, "A quantitative description of membrane current and its application to conduction and excitation in nerve", J. Physiol (Lond.), vol. 117, No. 4, pp. 500-544, 1952.

C. Guld, "A glass-covered platinuim microelectrode," Med. Electron. Biol. Engng. vol. 2, pp. 317-327, 1964.

K. D. Wise, J. B. Angell, and A.Starr, "An Integrated-Circuit Approach to Extracellular Microelectrodes", IEEE Transactions on Bio-medical engineering, vol. BME-17, No. 3, pp. 238-247, 1970.

M. Kuperstein, and D. Whittington, "A Practical 24 Channel Microelectrode for Neural Recording in Vivo", IEEE Transactions on Bio-medical engineering vol. BME-28, No. 3, pp. 288-293, 1981.

K. L. Drake, K. D. Wise, J. Farraye, D. J. Anderson, and S. L. Bement, "Performance of Planar Multisite Microprobes in Recording Extracellular Single-Unit Intracortical Activity", IEEE Transactions on Bio-medical engineering, vol. BME-35, No. 9, pp. 719-732, 1988.

D. R. Kipke, "Implantable neural probe systems for cortical neuroprostheses," Dig. IEEE Conf. Eng. Med. Biol., San Francisco, CA, Sep. 2004, pp. 5344-5347.

G. E. Perlin and K. D. Wise, "The effect of the substrate on the extracellular neural activity recorded with micromachined silicon microprobes," in Dig. IEEE Conf. Eng. Med. Biol., San Francisco, CA, Sep. 2004, pp. 2002-2005.

J. Ji, and K. D. Wise, "An implantable CMOS circuit interface for multiplexed microelectrode recording arrays," IEEE J. Solid-State Circuits 27 No. 3, pp. 433-443, 1992.

A. B. Frazier, D. P. O'Brien and M. G. Allen, "Two dimensional metallic microelectrode arrays for extracellular stimulation and recording of neurons," in 1993 IEEE Micro Electro Mechanical Systems Conf., Fort Lauderdale, FL, Feb. 7-10, p. 195-200.

Q. Bai and K. D. Wise, "A high-yield microassembly structure for three-dimensional microelectrode arrays" IEEE Trans. Biomed. Eng., vol. 47, No. 3, pp. 281-289, 2000.

D. A. Robinson, "The electrical properties of metal microelectrodes", Proc. IEEE, vol. 56, No. 6, pp. 1065-1071, 1968.

Y. Yao, M. N. Gulari, J. F. Hetke, and K. D. Wise, "A self-testing multiplexed CMOS Stimulating Probe for a 1024-site neural prosthesis", in Transducers '03: The 12th Internatianal Conference on Solid State Sensors, Anuators and Microsystems. Boston, MA, Jun. 8-12, 2003, pp. 1213-1216.

G.E. Perlin, A. M. Sodagar, and K. D. Wise, "Neural recording front-end designs for fully implantable neuroscience applications and neural prosthetic microsystems," in IEEE Int. Conf. Eng. Med. Biol., New York, Sep. 2006, pp. 2982-2985.

G. A. May, S. A. Shamma, and R. L. White, "A tantalum-on-sapphire microelectrode array," IEEE Trans. Electron Devices vol. ED-26, No. 12, pp. 1932-1939, 1979.

O. J. Prohaska, F. Olcaytug, P. Pfundner, H. and Dragaun, "Thin-film multiple electrode probes: Possibilities and limitations," IEEE Trans. Biomed. Eng. vol. BME-33, No. 2, pp. 223-229, Feb. 1986.

N. A. Blum, B. G. Carkhuff, H. K. R. L. Charles, Edwards, and R. A. Meyer, "Multisite microprobes for neural recordings", IEEE Trans. Biomed. Eng. vol. 38, No. 1, pp. 68-74, 1991.

S. A. Boppart, B. C. Wheeler, C. S. Wallace, "A Flexible Perforated Microelectrode Array for Extended Neural Recordings", IEEE Trans. Biomed. Eng. vol. 39, No. 1, pp. 37-42, 1992.

P. J. Rousche, D. S. Pellinen, D. P. Pivin Jr., J. C. Williams, R. J. Vetter, and D. R. Kipke, "Flexible polyimide-based intracortical electrode arrays with bioactive capability," IEEE Trans. Biomed. Eng., vol. 48, No. 3, pp. 361-371, 2001.

D. R. Kipke, D. S. Pellinen, R. J. Vetter, "Advanced neural implants using thin-film polymers", ISCAS 2002. vol. 4, pp. 173-176, 2002.

K. Lee, A. Singh, A., J. Heb, S. Massia, B. Kima, and G. Rauppc,"Polyimide based neural implants with stiffness improvement", Sensors and Actuators B, vol. 102, pp. 67-72, 2004.

K. K. Lee, J. P. He, A. Singh, S. Massia, G. Ehteshami, B. Kim, B. Kima, G. Rauppc, "Polyimide based intracortical neural implant with improved structural stiffness" J Micromech Microeng, vol. 14, pp. 32-37, 2004.

K. Lee, S. Massia, and J. He, "Biocompatible benzocyclobutene-based intracortical neural implant with surface modification", J. Micromech. Microeng., vol. 15, pp. 2149-2155, 2005.

J. A. Hosp, K. Molina-Lunab, B. Hertlera, C. O. Atiemoa, A. Stett, A. R. Luft, "Thin-film epidural microelectrode arrays for somatosensory and motor cortex mapping in rat", Journal of Neuroscience Methods, vol. 172, pp. 255-262, 2008.

J. W. Fawcett and R. A. Asher, "The glial scar and central nervous system repair", Brain Research Bulletin, vol. 49, No. 6, pp. 377-391, 1999.

P. J. Rousche, R. A. Normann, "Chronic recording capability of the Utah Intracortical Electrode Array in cat sensory cortex" Journal of Neuroscience Methods. vol. 82, pp. 1-15, 1998.

J. C. Williams R. L. Rennake, D. R. Kipke, "Long-term neural recording characteristics of wire microelectrode arrays implanted in cerebral cortex" Brain Res Protoc, vol. 4, pp. 303-313, 1999.

J. C. Williams, R. L. Rennaker, D. R. Kipke, "Stability of chronic multichannel neural recordings: implications for a long-term neural interface", Neurocomputing 26-27, pp. 1069-1076, 1999.

C. S. Bjornsson, S. J. Oh, Y. A. Al-Kofahi, Y. J. Lim, K. L. Smith, J. N. Turner, S. De, B. Roysam, W. Shain, S. J. Kim, "Effects of insertion conditions on tissue strain and vascular damage during neuroprosthetic device insertion", J. Neural Eng., vol. 3, pp. 196-207, 2006.

V. S. Polikov, P. A. Tresco, and W. M. Reichert, "Response of brain tissue to chronically implanted neural electrodes", J. of Neuroscience Methods, vol. 148, pp. 1-18, 2005.

A. Jackson and E. E. Fetz, "Compact movable microwire array for long-term chronic unit recording in cerebral cortex of primates", J. Neurophysiol., vol. 98, pp. 3109-3118, Sep. 2007.

J-M. Hsua, P. Tathireddy, L. Rieth, A. R. Norman, and F. Solzbacher, "Characterization of a-SiCx:H thin films as an encapsulation material for integrated silicon based neural interface devices" Thin Solid Films, vol. 516, No. 1, pp. 34-41, 2007.

X. Li, X. Wang, R. Bondokov, J. Morris, Y. H. An, T. S. Sudarshan, "Micro/Nanoscale Mechanical and Tribological Characterization of SiC for Orthopedic Applications", J Biomed Mater Res B Appl Biomater, vol. 72, No. 2, pp. 353-361, 2005.

(56) References Cited

OTHER PUBLICATIONS

U. Kalnins, A. Erglis, I. Dinne, I. Kumsars, S. Jegere, Clinical outcomes of silicon carbide coated stents in patient with coronary disease. Med. Sci. Monit., vol. 8, No. 2, pp. 16-20, 2002.

R. Yakimova, R. M. Petoral Jr., G. R. Yazdi, C. Vahlberg, A. Lloyd Spetz, and K Uvdal, "Surface functionalization and biomedical applications based on SiC", J. Phys. D: Appl. Phys., vol. 40, pp. 6435-6442, 2007.

C. Coletti, M. J. Jaroszeski, A. Pallaoro, A. M. Hoff, S. Iannotta, and S. E. Saddow, "Biocompatibility and wettability of crystalline SiC and Si surfaces", in 29th Annual IEEE EMBC Proceedings, Aug. 23-26, 2007, pp. 5849-5852.

C. L. Frewin, M. Jaroszeski, E. Weeber, K.E. Muffly, A. Kumar, M. Peters, A. Oliveros, and S.E. Saddow, "Atomic Force Microscopy Analysis of Central Nervous System Cell Morphology on Silicon Carbide and Diamond Substrates", Journal of Molecular Recognition, vol. 22: 380-388, 2009.

International Search Report for PCT/US2010/058376 (filed of Nov. 30, 2010) with a mailing date of Aug. 19, 2011, Applicant: University of South Florida et al.

\* cited by examiner

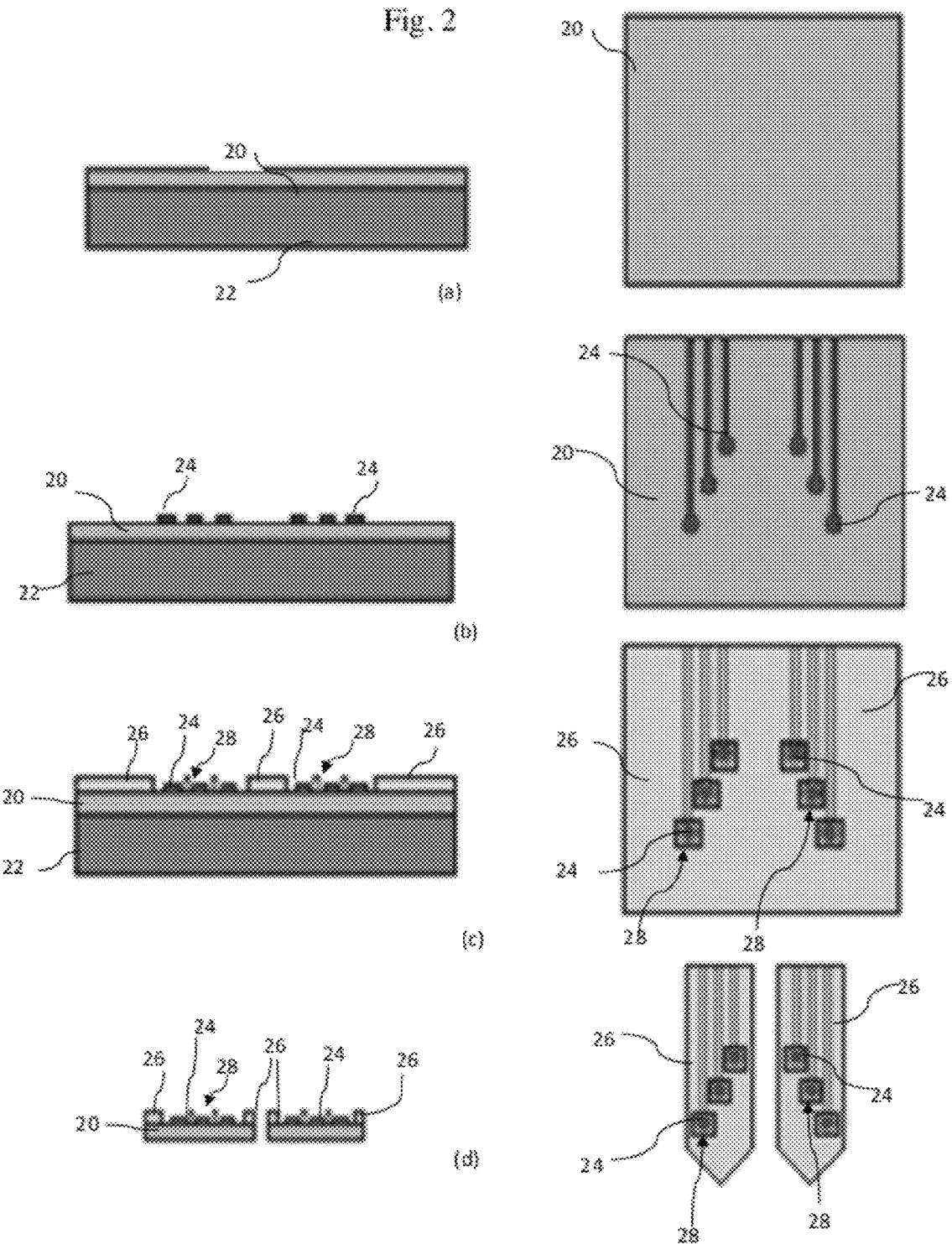

CUBIC SILICON CARBIDE IMPLANTABLE NEURAL PROSTHETIC

CROSS REFERENCE TO RELATED APPLICATIONS

This application is a continuation of International Application No. PCT/US2010/058376, entitled "Cubic Silicon Carbide Implantable Neural Prosthetic," filed on Nov. 30, 2010, which claims priority to U.S. Provisional Patent application No. 61/265,148, entitled "Cubic silicon carbide as a biocompatible material for the construction of planar neural prosthetic," filed on Nov. 30, 2009, the contents of which are hereby incorporated by reference.

BACKGROUND OF THE INVENTION

1. Field of the Invention

This invention relates to the field of medical devices. More specifically, it relates to an implantable neuronal prosthetic and method of manufacture thereof comprised of biocompatible cubic silicon carbide.

2. Description of the Prior Art

The brain machine interface (BMI) offers therapeutic options to relieve many individuals suffering from central nervous system (CNS) or peripheral nervous system (PNS) disabilities due to disease or trauma. The central component of the BMI system is the neuronal prosthetic which interacts within the brain with the body's electrophysiological signals. Implantable neuronal prosthetics have the ability to receive electrical signals directly from neurons or muscles and to deliver electrical signals to these same cells, providing a means for a closed loop BMI systems. These devices are unfortunately still regulated to experimental BMI systems due to a severe long term in vivo reliability issue. Specifically, device failure over time is thought to arise from lowered material biocompatibility that activates the immune response of the body. For example, the "foreign body" response from the support cells in the CNS, the glia, escalates the levels of harsh chemicals in the implant area and leads to the eventual encapsulation of the device. Not only is the glial response unsuitable, but BMI electrode devices are extremely vulnerable to changes in impedance, and the resulting encapsulation cause the devices to fail within months after encapsulation.

Accordingly, what is needed is an implantable neuronal prosthetic and method of manufacture thereof that is capable of being implanted in the body for extended periods of time without failure. However, in view of the prior art considered as a whole at the time the invention was made, it was not obvious to those of ordinary skill how to provide such a neuronal prosthetic.

SUMMARY OF THE INVENTION

Generally speaking, the claimed invention is an implantable neuronal prosthetic and method of manufacture thereof for placement in a brain of a patient for receiving and sending electrical signals. The implantable neuronal prosthetic includes at least one elongated electrode shank formed form a single crystal cubic silicon carbide that is adapted for arrangement in the brain. Single crystal cubic silicon carbide is a biocompatible, chemically inert, physically strong and elastic semiconducting material. At least one electrode contact is disposed on the surface of the at least one elongated electrode shank and is arranged to electrically couple with the brain. The at least one electrode contact is formed of a conductive material, such as, for example, gold, platinum, platinum-iridium alloys, iridium oxide, stainless steel, tungsten, or titanium nitride.

An insulation layer consisting of amorphous, polycrystalline, or low temperature deposited crystalline silicon carbide is disposed over the elongated electrode shank. The silicon carbide insulation layer is removed from the active area of at least one electrode contact. Signal control electronics are attached to the at least one elongated electrode shank and are in electrical continuity with the at least one electrode contact.

In an embodiment, a plurality of the elongated electrode shanks is arranged into a matrix.

The implantable neuronal prosthetic interacts directly with single or small groups of targeted neurons within the CNS or PNS. The prosthetic uses the chemical-ionic interaction between the electrodes and the extracellular electrolyte media of the CNS/PNS to electrically stimulate neurons and, in turn, receive the electrochemical signals they generate. The prosthetic serves as a prime component for an implantable BMI that is used to bridge neural signals over damaged areas, transport signals from the brain to an external machine, or receive signals from a sensor or similar device and transport them directly to neurons within the CNS.

BRIEF DESCRIPTION OF THE DRAWINGS

For a fuller understanding of the invention, reference should be made to the following detailed description, taken in connection with the accompanying drawings, in which:

FIG. 2(a) depicts the method of manufacturing an implantable neuronal prosthetic;

FIG. 2(b) depicts the method of manufacturing an implantable neuronal prosthetic;

FIG. 2(c) depicts the method of manufacturing an implantable neuronal prosthetic; and FIG. 2(d) depicts the method of manufacturing an implantable neuronal prosthetic.

DETAILED DESCRIPTION OF THE PREFERRED EMBODIMENT

Figure 1:
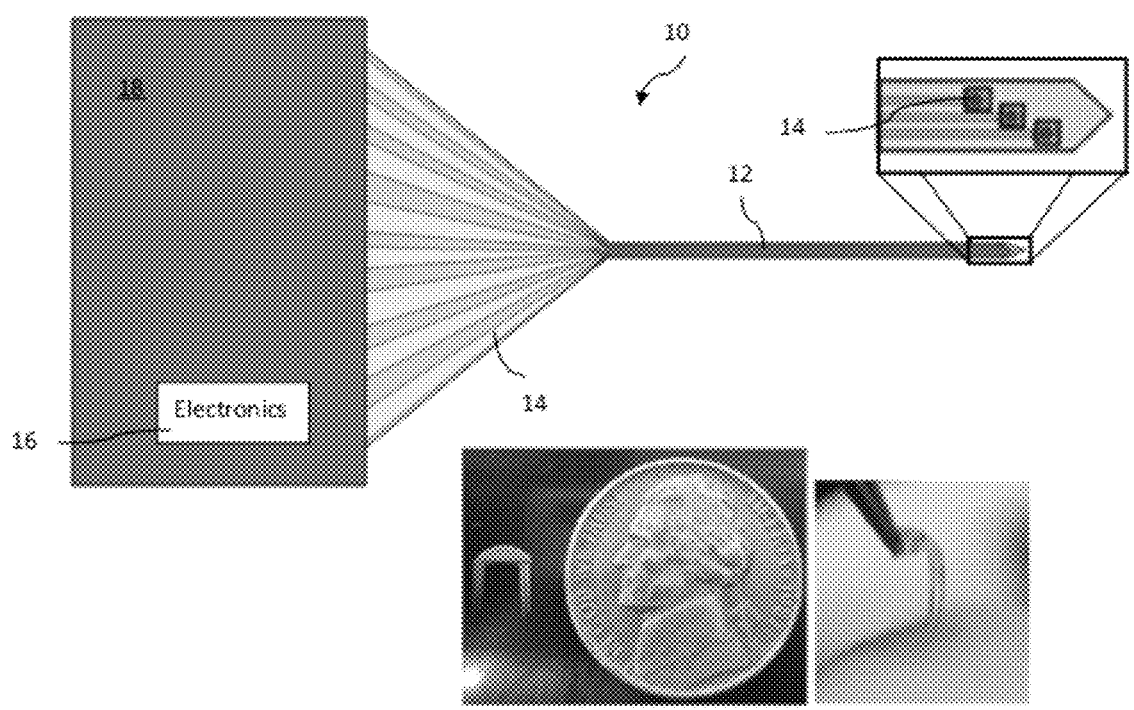
FIG. 1 is an abstract representation of an implantable neuronal prosthetic, with the base of the shank exploded to show details and an inset showing a manufactured 3C—SiC shank and with 2 photographs of 3C—SiC shanks constructed with the processes named in this invention.

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

The claimed invention includes an implantable neural prosthetic having a shank formed of cubic silicon carbide (also referred to as β-SiC or 3C—SiC). Cubic silicon carbide is a biocompatible material that prevents encapsulation of the neural prosthetic due to glial response. It has immense material strength that enables the prosthetic to be less invasive; it also has excellent elasticity for a semiconductor material, which combats problems with micro-motion, and can be grown on Si, which allows for direct integration with the electronics required for signal processing and generation.

The claimed invention also includes electrode contacts disposed on the surface of the cubic silicon carbide shank. The electrode contacts are formed of any suitable conductive material; for example, the electrode contacts may be formed from the group consisting of gold, platinum, platinum-iridium alloys, iridium oxide, stainless steel, tungsten, titanium nitride, or other suitable material.

As depicted in FIG. 1, the general design for the implantable neural prosthetic is denoted as numeral 10. The implantable neural prosthetic 10 includes a shank 12 formed on the base material, cubic silicon carbide. The shank 12 includes electrodes 14 deposited on its surface. Electronics 16 for signal generation, switching control, signal filtering, digitization, wireless transmission, and power control are disposed on Si base 18, which is connected to shank 12. Si is used for the device circuitry due to the fact that the architectures required for their construction are well known in industry and much easier to accomplish in Si than in the chemically resistant and hard SiC material. Amorphous SiC is deposited over the Si Electronics 16 to hermetically seal and protect them from the harsh body environment. An insulating layer consisting of amorphous SiC, polycrystalline SiC, or low temperature crystalline SiC is also deposited over the electrodes 14, with portions of the insulating SiC removed around the electrode 14 to allow the electrodes 14 to be in direct contact with the neuronal environment.

Multi-shank devices may be constructed on a single wafer and these multi-shank planar constructions can be joined into a matrix.

The method of manufacture of the cubic silicon carbide neural prosthetic 10 is shown in FIG. 2(a)-2(d). The process begins with the chemical vapor deposition (CVD) growth of cubic silicon carbide 20 on a Si substrate wafer 22, as shown in FIG. 2A. In an embodiment, the cubic silicon carbide is grown in a two stage process. The wafer is placed in a chemical vapor deposition reactor which is purged and evacuated of gasses. Hydrogen and a carbon precursor, such as propane, are introduced into the chamber, which is heated by RF induction of a graphite susceptor to a temperature of 1150-1250° C. This temperature is held constant for five minutes to allow carbon to react and bind with silicon to form a cubic silicon carbide template layer. The temperature is then increased and a Si precursor, such as silane, is added to the gas flow. Heating continues until the temperature approaches the melting point of Si (1410° C.) and is held constant just under the Si melting point (1385-1390° C.), which allows continued growth of the cubic silicon carbide crystal film. When the process is complete, heating is removed and the wafer is cooled in Ar gas. In this embodiment, the device uses a 10-25 μm thick films of cubic silicon carbide.

As shown in FIG. 2(b), the cubic silicon carbide 20 and Si wafer 22 are cleaned and patterned for electrode deposition using standard ultraviolet photolithography techniques. Electrodes 24 can be any biocompatible conductive material like gold, platinum, platinum-iridium alloys, iridium oxide, stainless steel, tungsten, or titanium nitride. Electrode deposition can be accomplished using various semiconductor industry techniques like electron beam heating deposition, sputter deposition, cathodic arc deposition, physical vapor deposition (PVD), or CVD. The electrodes 24 require an insulating coating which prevents charge bleed over the length of the electrode 24 and reduces cross talk between electrodes 24.

Amorphous SiC 26, as shown in FIG. 2(c), is used as the insulating material. This material is deposited by plasma enhanced chemical vapor deposition (PECVD) at low temperature (150-450° C.). For electrodes which can withstand higher temperatures, electrodes can be insulated with polycrystalline SiC (deposition at temperatures lower than approximately 800° C.) or intrinsic single crystalline SiC (deposition temperatures above 800° C.). Windows 28 are opened around the electrodes 24 at the end of the shank to allow for the generation of the extracellular cerebral spinal fluid/electrode electrolysis connection. This is accomplished on the device by protection with photolithographic polymers or metals and then using deep reactive ion etching (DRIE) to remove the insulating SiC 26 above the electrodes 24 so they can form contact with target neurons in the CNS/PNS.

As shown in FIG. 2(d), photolithography is used to deposit a combination of polymers and a metal which are used to generate the shank as well as preserve the completed electrode surface during further processing. DRIE etches through the exposed insulating 26 and base 3C—SiC 20, stopping at the Si 22 layer to form the sidewalls of the shank. The wafer is reversed, placing the electrode side onto a handle wafer, and the Si base wafer 22 is completely removed using either wet anisotropic etching (potassium hydroxide (KOH)) or DRIE etching. This process produces the released, freestanding 3C—SiC electrode and shanks, which are then cleaned of the protective metal and polymer coating.

The completed shank devices are attached to electronics to facilitate signal transmission and recording. A fully-implantable device includes electronics for conditioning and amplifying received signals (via amplifiers/filters, etc.), signal generation to excite an action potential from neurons or muscles (transmission), a control system to manage the signals, wireless communication, and power management. Power for the device can be either delivered with rechargeable batteries and/or inductive wireless generation. Although electronics can be generated in 3C—SiC, they can more easily be realized in Si. The latter method implies that Si electronics are realized separately and then attached (both electrically and physically) to the 3C—SiC device structure through standard semiconductor die bonding techniques. The vulnerable Si electronics are then hermetically sealed with a chemically resistive, low temperature deposition, biocompatible material, like amorphous silicon carbide, to protect it from attacks from the body's immune system. An alternative method to facilitate the onboard electronics. One way to archive this goal is to preserve part of the Si substrate upon which the 3C—SiC was grown upon for electronics implementation. The required electronics are realized in the preserved silicon tab portion of the shanks and connected to the 3C—SiC shank and electrodes through interconnections made using standard microelectronic processing (metal traces, insulation, conductive via connections, etc.). The device, consisting of signal and power electronics and at least one implantable shank with at least one electrode, can be used as the main interface component of a brain machine interface (BMI) device.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall there between.

What is claimed is:

1. An implantable neuronal prosthetic for placement in a brain of a patient for receiving and sending electrical signals, comprising:

at least one elongated electrode shank adapted for arrangement in the brain having at least one electrode contact disposed on its surface and arranged to electrically couple with the brain, the at least one elongated electrode shank being formed from a single crystal cubic silicon carbide.

2. The implantable neuronal prosthetic of claim 1, further comprising:
the at least one electrode contact being formed from the group consisting of gold, platinum, platinum-iridium alloys, iridium oxide, stainless steel, tungsten, and titanium nitride.

3. The implantable neuronal prosthetic of claim 1, further comprising:
an insulation layer of amorphous, polycrystalline, or single crystal silicon carbide disposed over the elongated electrode shank, the insulation layer of amorphous, polycrystalline, or single crystal silicon carbide being removed from the at least one electrode contact.

4. The implantable neuronal prosthetic of claim 1, further comprising:
signal control electronics attached to the at least one elongated electrode shank and in communication with the at least one electrode contact.

5. The implantable neuronal prosthetic of claim 1, further comprising:
a plurality of the at least one elongated electrode shanks being arranged into a matrix.

6. A method of manufacturing an implantable neuronal prosthetic for placement in a brain of a patient for receiving and sending electrical signals, comprising the steps of:
forming at least one elongated electrode shank adapted for arrangement in the brain out of a single crystal cubic silicon carbide; and
forming at least one electrode contact on a surface of at least one elongated electrode shank, the at least one electrode being arranged to electrically couple with the brain.

7. The method of claim 6, wherein the at least one electrode contact is formed from the group consisting of gold, platinum, platinum-iridium alloys, iridium oxide, stainless steel, tungsten, and titanium nitride.

8. The method of claim 6, further comprising the steps of:
insulating the at least one elongated electrode shank with amorphous, polycrystalline, or single crystal silicon carbide; and
removing the insulating layer of amorphous, polycrystalline, or single crystal silicon carbide from the at least one electrode contact such that the at least one electrode contact is exposed.

9. The method of claim 6, further comprising the step of:
attaching signal control electronics to the at least one elongated electrode shank, the signal control electronics being in communication with the at least one electrode contact.

10. The method of claim 6, further comprising the step of:
arranging a plurality of the at least one elongated electrode shanks into a matrix.

\* \* \* \* \*